(12) United States Patent
Kuehl (10) Patent No.: US 10,646,367 B2
(45) Date of Patent: May 12, 2020

(54) DISPOSABLE TAPE KIT AND METHOD FOR WRIST IMMOBILIZATION

(71) Applicant: Mueller Sports Medicine, Inc., Prairie du Sac, WI (US)

(72) Inventor: Sarah Kuehl, Madison, WI (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 442 days.

(21) Appl. No.: 15/238,786

(22) Filed: Aug. 17, 2016

(65) Prior Publication Data

US 2017/0049602 A1 Feb. 23, 2017

Related U.S. Application Data

(60) Provisional application No. 62/208,237, filed on Aug. 21, 2015.

(51) Int. Cl.
*A61F 5/05* (2006.01)
*A61F 5/01* (2006.01)
(Continued)

(52) U.S. Cl.
CPC ........ *A61F 5/0118* (2013.01); *A61F 5/05866* (2013.01); *A61F 13/0273* (2013.01); *A61F 13/104* (2013.01)

(58) Field of Classification Search
CPC .......... A61F 13/00055; A61F 13/00042; A61F 13/00051; A61F 13/00987;
(Continued)

(56) References Cited

U.S. PATENT DOCUMENTS 3,971,374 A * 7/1976 Wagner ................. A61F 13/104
602/58
6,191,337 B1 * 2/2001 Himmelsbach ....... A61F 5/0118
602/41

(Continued)

OTHER PUBLICATIONS

THERATAPE "Kindmax Precut Wrist Tape" theratape.com, published on Feb. 6, 2015 (Feb. 6, 2015), retrieved on Oct. 21, 2016 (Oct. 21, 2016), accessed at https://web.archive.org/web/20150206153017/http:/www.theratape.com/kindmax-precut-wrist-support.hlml#>, entire document, especially p. 3 Upper Image; p. 4 "Product Specs"; p. 4 "Additional Info".

(Continued)

*Primary Examiner* — Anna K Kinsaul
*Assistant Examiner* — Camtu T Nguyen
(74) *Attorney, Agent, or Firm* — Rick L. Abegglen (57) ABSTRACT

A disposable tape kit and method for use by athletes or others requiring immobilisation of the wrist. The tape kit includes a first strip with a palm anchor, an anterior wrist portion, and an anterior forearm anchor, along with a second strip that includes a back anchor, a wrist anchor starting end, a wrist anchor central portion, and a wrist anchor finishing end. When applied to a wearer's hand, wrist, and forearm, tension along the first strip on the anterior side of the wrist resists extension of the wrist, while tension along the second strip on the posterior side of the wrist resists flexion of the wrist. The combination of the first tension and second tension tends to immobilize the wrist against both flexion and extension.

12 Claims, 11 Drawing Sheets

(51) Int. Cl.
*A61F 5/058* (2006.01)
*A61F 13/02* (2006.01)
*A61F 13/10* (2006.01)

(58) Field of Classification Search
CPC ........ A61F 2013/00429; A61F 13/0273; A61F 13/104; A61F 5/0118; A61F 5/05866; A61F 5/05875
See application file for complete search history.

(56) References Cited

U.S. PATENT DOCUMENTS

| | | | |
|---|---|---|---|
| 7,393,334 B2 * | 7/2008 | Tornai | A61F 5/0118 602/20 |
| 8,261,162 B2 | 7/2012 | Bushby | |
| 8,414,511 B2 | 4/2013 | Bushby | |
| 2013/0218060 A1 | 8/2013 | Bushby | |
| 2014/0081188 A1 * | 3/2014 | Hargis | A61F 5/0118 602/7 |
| 2014/0373247 A1 | 12/2014 | Swaby | |

OTHER PUBLICATIONS

Kindmax Healthcare Corporation "Precut Kinesiology Tape", kindmax.com, published on Feb. 6, 2015 (Feb. 6, 2015), retrieved on Oct. 21, 2016 (Oct. 21, 2016), accessed at <http://www.theratape.com/downloads/dl/file/id/65/product/735/kindmax_wrist_support_application_instructions.jpg>.

Acti-Tape "Acti-Tape—Wrist—Carpal Tunnel" youtube.com, published on Dec. 28, 2011 (Dec. 28, 2011), retrieved on Oct. 21, 2016 (Oct. 21, 2016), accessed at <https:///www.youtube.comlwatch?v=I-MXfQ41X68>, entire document.

KT Tape "KT Tape: Carpal Tunnel", youtube.com, published on Jan. 19, 2010 (Jan. 19, 2010), retrieved on Oct. 21, 2016 (Oct. 21, 2016), accessed at <https://www.youtube.comlwatch?v=FAWu0_SWDhM>, entire document.

Mueller "CT Tape" muellersportsmed.com, published on Oct. 21, 2016 (Oct. 21, 2016), retrieved on Oct. 21, 2016 (Oct. 21, 2016), accessed at <http://www.muellersportsmed.com/carpal-tunnel-tape.html>. entire document.

* cited by examiner

DISPOSABLE TAPE KIT AND METHOD FOR WRIST IMMOBILIZATION

CROSS REFERENCE TO RELATED APPLICATIONS

This application claims priority to provisional application No. 62/208,237 filed Aug. 21, 2015, the disclosure of which is incorporated herein by reference in its entirety for continuity of disclosure.

FIELD OF THE INVENTION

This invention relates generally to the field of articles worn by persons to promote healing and/or to reduce the likelihood, severity, or exacerbation of injury to the body, and more specifically to the field of devices used to immobilize the wrist.

BACKGROUND OF THE INVENTION

A variety of medical conditions and injuries benefit from immobilization of the wrist during vigorous physical activity (such as competitive sports) and/or during normal daily activities. Carpal tunnel syndrome, for example, is a painful progressive condition caused by compression of a key nerve in the wrist. Tennis elbow (lateral epicondylitis) is another painful chronic condition (manifesting in the elbow instead of in the wrist) that arises from an acute or chronic inflammation of the tendons that join the forearm muscles on the outside of the elbow (lateral epicondyle). These conditions, and others, may benefit from wrist immobilization to promote healing and to protect injured tissues or ligaments.

Wrist braces formed of fabric to fit the hand and wrist, with a rigid or semi-rigid splint in the palm, have been used to immobilize the wrist for many years. Wrist braces are often bulky, so they may not fit in the sleeve of the wearer's normal shirt or jacket. Wrist braces may prevent the use of gloves in cold weather or to protect the wearer's hands against contamination or injury. Wrist braces often block perspiration, trapping sweat to cause discomfort in the wearer and deterioration/odors in the brace itself. Wrist braces may interfere with finger movement, reducing manual dexterity and making it difficult to perform tasks such as writing, typing, or grasping needed for work activities or to perform tasks of daily living.

For these reasons, there has long been motivation to find an improved device for wrist immobilization that can avoid or reduce undesirable aspects of prior art devices such as poor performance, bulk, weight, moisture retention, difficulty of application, fit, cost, and/or appearance.

DEFINITION OF TERMS

The following terms, as used herein, have the following meanings.

With regard to materials, a "woven" fabric is that class of fabrics wherein involves the interlacing or interweaving of two sets of threads at right angles (perpendicular) to each other: the warp (lengthwise threads) and the weft (crosswise threads inserted over-and-under the warp threads). A woven fabric only stretches in the bias directions (45 degrees to its warp and weft threads). In contrast, a "non-woven" fabric is that class of fabrics wherein fibers or threads are matted together, usually in a random or non-directional manner, and are not held in place by interweaving. Felt and cardboard are examples of non-woven materials. One important technical difference between a woven and non-woven fabric is their tensile strength (i.e., resistance to elongation). Woven fabrics can have much higher tensile strength and resistance to deformation or elongation than that of non-woven fabric of the same GSM (Grams per Square Meter). The GSM is a scale for the weight of the sheet of fabric, paper, etc., which also provides some indication of its thickness. The term "microfiber" commonly refers to any fiber with strands less than 1 denier, or about half as thick as a strand of silk. Some microfiber fabrics use strands that are only 10 microns in diameter, or about one-tenth as thick as a human hair. "Denier" is the unit of measure for fibers that indicates their fineness.

With regard to thickness, the term "mil" is a unit of length or thickness, equal to one one-thousandth ($1/1000$) of an inch or 0.001". For example, 2 mils is equal to 0.002" ($2/1000$"). A "mil" is not the same as a "millimeter". In contradistinction, the term "millimeter", abbreviated "mm", is a unit of length or thickness, equal to one-thousandth of a meter or equal to thirty-nine thousandths ($39/1000$) of an inch. For example, 1 mm is equal to 0.039370 inches (approximately $3/64$"), and 2 mm is equal to 0.078740 inches (approximately $5/64$"). 1 mil is equal to 0.0254 millimeters (mm), and 1 millimeter (mm) is equal to 39.37007874 mils. As an example to compare the different thickness measurements; a sheet of standard 20 lb wt. copy paper and a common postage stamp are each about 0.1 mm (equal to 4 mils or 0.004 inches) thick, and a conventional postcard is approximately 0.178 mm (equal to 7 mils or 0.007 inches) thick.

With regard to material properties, the terms "resilient" and "elastic" refer to a material capable of regaining its original shape or position after being deformed elastically such as by bending, stretching, compression, or other deformation. "Deformation" is an alteration of shape, as by pressure or stress. "Resilience" is the capability of a strained body to recover its size and shape after deformation caused especially by compressive stress. The term "elasticity" is the physical property of a material that returns to its original shape after the stress (e.g. external forces) that made it deform is removed. The relative amount of deformation is called the "strain". The term "elongation" means the state of being elongated or lengthened. The term "stretch" means the elongation, lengthening, widening, or distending of a material under an applied load.

The term "modulus of elasticity" is the mathematical description of an object or substance's tendency to be deformed elastically (i.e., non-permanently) when a force is applied to it, more particularly, the ratio of the stress applied to a material to the resulting strain within the elastic limit, also known as "elastic modulus" or "tensile modulus". The term "tensile strength" is the measure of the ability of material to resist a force that tends to pull it apart. It is expressed as the minimum "tensile stress" (force per unit area) needed to split the material apart. Dimensions measured in the cross-machine (CD) direction are referred to as "width" dimension, while dimensions measured in the machine direction (MD) are referred to as "length" dimensions.

With regard to pressure sensitive adhesives ("PSA" or plural "PSAs"), the term "tack" is the property of an adhesive that enables it to instantly form a bond when brought into contact with another surface. The term "tack force", also called "tack strength", is the maximum force required to separate the bonded surfaces. "Adhesion" (peel adhesion), refers to how well the tape sticks to a surface, and can be measured in ounces of pull (force) required to remove a one-inch wide strip of tape from a steel plate (i.e., adhesion to steel) using units of ounces/inches. "Peel strength" is measured as a force required to remove a standard PSA strip from a specified test surface under a standard test angle (e.g., 90° or 180°) under standard conditions. PSAs may be "removable" or "permanent". "Low-tack" adhesives have low adhesion properties and are easily applied and removed (i.e. the adhesive used on the adhesive note paper sold under the mark POST-IT®) and generally can not support much weight. "Medium-tack" adhesives have high adhesion properties but are removable and repositionable. "High-tack" adhesives are typically considered to be a relatively permanent bonding adhesive. Foil tape for HVAC duct work is an example of a permanent adhesive application.

The ASTM (the American Society for Testing and Materials), now named ASTM International, is an international standards organization that develops and publishes technical standards and testing methods for a wide range of materials, including various classes of pressure sensitive adhesive tapes. Such testing methods include Peel Adhesion, Shear Adhesion, Tensile Strength, Breaking Strength, Elongation, etc. For example, the average tensile strength in both the machine and cross-machine directions of each roll of tape shall be not less than 25 lbs/in (4.37 N/mm) of width; the average peel adhesion strength of each roll of tape shall be not less than 3.75 lbs/in (0.66 N/mm) of width. The average peel adhesion strength at a 180° angle of each roll of tape shall be not less than 3.75 pounds per inch (0.66 N/mm) of width of tape.

With regard to medical devices, a "splint" is commonly understood to mean a rigid or flexible appliance for fixation of displaced or movable parts of the human body, in other words an orthopedic device for immobilization, restraint, or support of any part of the human body. A splint may be rigid or flexible. An "orthopedic brace", also known as an "orthosis" or "orthotic", is commonly understood to mean a device used to immobilize a joint or body segment, restrict movement in a given direction, assist movement generally, reduce weight bearing forces for a particular purpose, or otherwise correct the shape and/or function of the body to provide easier movement capability or reduce pain.

As used herein in conjunction with the present invention, the term "orthotic" means a device for supporting and immobilizing a weak or injured joint or body segment, restricting movement in a given direction, assisting movement generally, reducing weight bearing forces, and improving the function of the joint or body segment to provide easier movement capability or reduce pain. The term "strap" means a long narrow flat strip of a flexible material used for securing, holding together, or wrapping. The term "disposable" means for use in a single continuous one-time application and treatment followed by removal and disposal, rather than for removal and re-use for additional or multiple applications. The term "non-resilient" means a non-cushioning material not capable of being deformed elastically, elongated, lengthened, widened, or distended by stretching or compressed by pressure or stress under an applied load. The term "inelastic" means a material not capable of being deformed elastically, elongated, lengthened, widened, or distended by stretching under an applied load or stress. The term "flexible" means capable of conforming to the shape and contours of the surface to which it is applied, and being flexed repeatedly without damage.

As used herein in conjunction with the present invention, the term "non-stretch" woven material means a woven material wherein both the warp (lengthwise) and weft (crosswise) threads are substantially inelastic; consequently, the fabric material is substantially non-stretchable beyond its original dimensions in a longitudinal and transverse direction. More specifically, a woven material which exhibits between 0% to 3% elongation along its longitudinal and transverse axis during normal use is a "non-stretch" woven material. The term "preformed" as used herein in conjunction with the present invention, refers to an object that has been formed during its manufacture into the condition or shape in which it is intended to be used prior to its use by an end user. This is in contrast to a sheet, strip, or roll, of material which requires cutting or shaping by an end user prior to its use.

As used herein in conjunction with the present invention, the term "mil" means a unit of length or thickness, equal to one one-thousandth (¹/₁₀₀₀) of an inch or 0.001". 1 "mil" is equal to 0.0254 millimeters (mm) and thus is significantly smaller than 1 "mm", and should be clearly distinguished over the terms "millimeter" and "mm", which is a unit of length or thickness, equal to one-thousandth of a meter or equal to thirty-nine thousandths (³⁹/₁₀₀₀) of an inch. 1 "mm" or "millimeter" is equal to 39.37007874 "mils", or 0.039370 inches (approximately ³⁄₆₄") and, thus, is significantly larger than 1 "mil". As used herein in conjunction with the present invention, the term "ultrathin" means very thin; more specifically having a thickness less than 1 mm (less than 0.0394 inches).

SUMMARY OF THE INVENTION

In a first embodiment, a tape kit for wrist immobilation includes a first non-stretch adhesive strip on release backing with a palm anchor portion, an anterior wrist portion, and an anterior forearm anchor; and a second adhesive strip on release backing with a back anchor and a wrist anchor sized to fit and wrap around the wrist area of a person.

In a second embodiment, a method of using a tape kit for wrist immobilization includes steps of (A) providing the above-described tape kit; (B) adhering the palm anchor of the first strip to the wearer's palm; (C) adhering the anterior forearm anchor of the first strip to the wearer's anterior forearm; (D) adhering the back anchor of the second strip to the wearer's hand-back and adhering the wrist anchor starting end to the wearer's posterior wrist area; and (E) wrapping the second strip around the wearer's wrist to adhere the wrist anchor central portion and wrist anchor finishing end about the wearer's wrist.

A tape kit and method according to the invention may include a palm anchor or a back anchor with a greater number of anchor segments. A tape kit and method may include a second strip made of a different material compared to the first strip, for example the second strip may be a cohesive material (instead of an adhesive) or it may be elastic instead of inelastic to promote comfort and adjustability during use.

Further objects, features, and advantages of the invention will be apparent from the following detailed description when taken in conjunction with the accompanying drawings.

DETAILED DESCRIPTION OF THE INVENTION

Figure 1A:
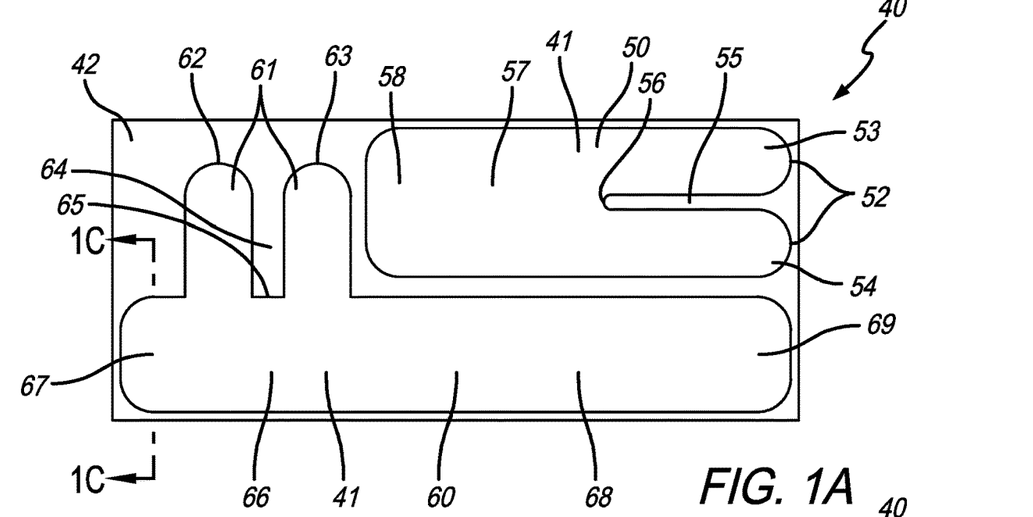
FIG. 1A is a plan view of a disposable tape system for wrist immobilization according to the invention, laid flat to expose the front (exterior) surface of the tape system.
Figure 1B:
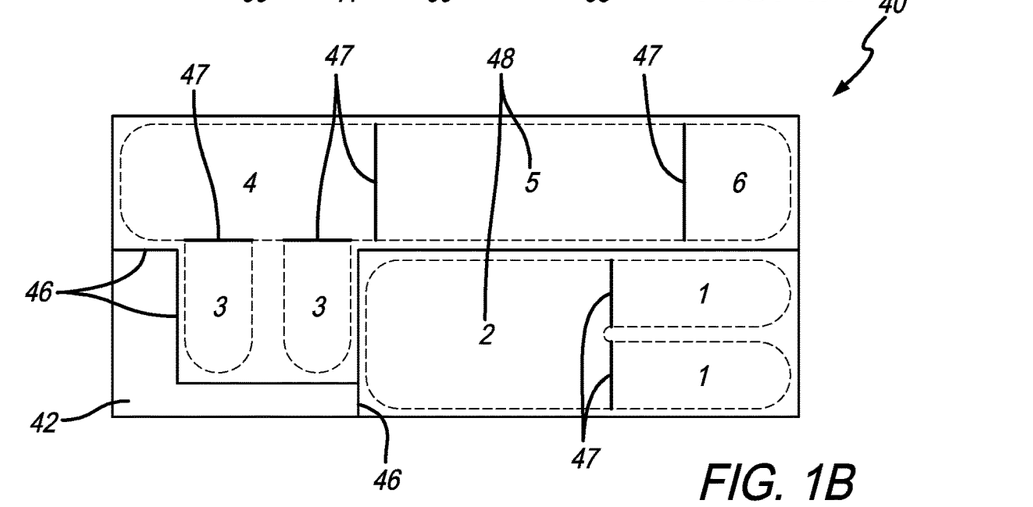
FIG. 1B is a plan view of the tape system of FIG. 1A, laid flat to expose the back (posterior) surface of the tape system, in other words the release layer bearing the tape prior to application to the wearer.
Figure 1C:
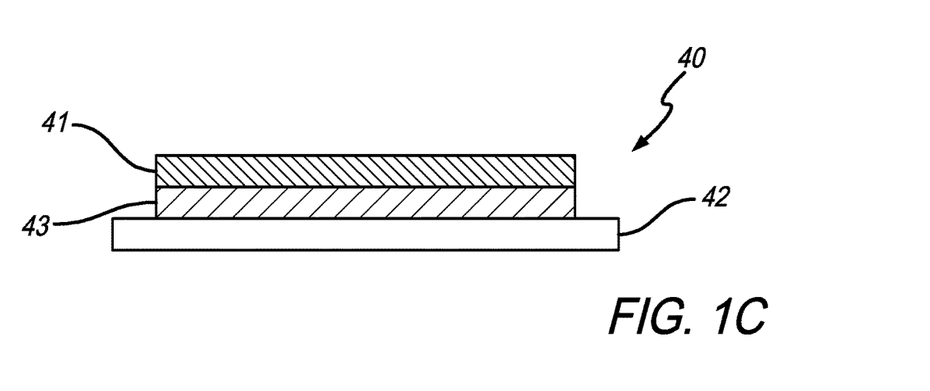
FIG. 1C is a cross-section of the tape system of FIG. 1A taken along the line 1C-1C thereof.

Referring to the drawings, FIGS. 1A-1C show a disposable tape system, indicated generally at 40, for wrist immobilization according to the invention, before the tape system is applied to the wearer. FIG. 1A shows the front (exterior) surface and FIG. 1B shows the back (posterior) surface of the tape system 40. As perhaps best shown in the cross section of FIG. 1C, the tape system 40 can be of conventional construction for bandages and tapes made to adhere to the human body. The tape system 40 typically comprises multiple precut portions of sheet material 41 covered with a layer of adhesive 43 and mounted a release backing 42, for example a first strip 50 and a second strip 60. Although in a preferred embodiment the same sheet material 41 is used for the first strip 50 and the second strip 60, that is not required and (for example) the first strip 50 might be made of a non-elastic adhesive material and the second strip 60 might be made of a different, perhaps elastic and/or cohesive (material that sticks to itself but not to skin or hair), material.

The sheet material 41 is preferably made of an ultrathin and inelastic yet flexible woven sheet material, such as a rayon microfiber where both the warp (lengthwise) and weft (side-to-side) fibers are both substantivally inelastic. The sheet material 41 preferably has a thickness less than 1 mm; preferably in a range of between about 5 mils (0.127 mm or 0.005 inch) to about 30 mils (0.762 mm or 0.030 inch), and most preferably less than 15 mils (0.381 mm or 0.015 inch). The sheet material 41 preferably has a tensile strength in excess of 70 lb/in-width and a ratio of elongation-to-tensile strength that is less than nine tenths (0.9) to provide a balanced combination of strength and resistance to elongation. The sheet material 41 is preferably breathable and porous, with a moisture vapor transfer rate (MVTR) of at least 100 grams per square meter over 24 hours, and is preferably hypo-allergenic. It should be understood that other flexible non-resilient non-stretch woven materials having these same or substantially the same physical properties may be used.

The adhesive 43 is preferably a high holding strength adhesive of sufficient tack strength so as to adhere the first strip 50 and secodn strip 60 to the wearer's hand and wrist during use but allow them to be removed without damage to the user's skin, such as an adhesive having a 180° peel strength equal to, or greater than, 15 oz/in when tested in accordance with the Pressure Sensitive Tape Council (PSTC) PSTC-3 Standard Adhesion to Steel 180° Peel Test. The adhesive 43 is preferably hypo-allergenic and non-irritating to the skin, and is thin—preferably less than 3.5 mils (0.0889 mm or 0.0035 inch) thick. An adhesive 43 with these properties can enable removal and readjustment of the tape strips by pulling the strips away from the skin surface at a ninety-degree angle, while remaining highly resistant to shear stresses to prevent slip or creep of the strips while applied to the skin of the wearer during use.

The combination of the sheet material 41 and adhesive layer 43 should be thin—less than 1 mm, preferably in a range of between about 5 mils (0.127 mm or 0.005 inch) to about 30 mils (0.762 mm or 0.030 inch), and most preferably less than 15 mils (0.381 mm or 0.015 inch).

The release backing 42 can be formed of thin paper or plastic film coated on one side with a release agent, for example silicone, for example, a 3.5 mil 60 lb. release liner paper sold under the trademark KRAFT®. The adhesive side of the first strip 50 and second strip 60 can be mounted on the coated side of the release backing 42.

As perhaps best shown in FIG. 1B which shows the release backing, the multiple precut portions in the tape system 40 may be conveniently manufactured on a single sheet of release backing 42, and then separated, or made tearable, into individual pieces for application using one or more perforations or full or partial die cuts 46 in the release backing 42. The release backing 42 may also include one or more perforations or full or partial die cuts 47, so that specific portions of the release backing may be removed to expose particular areas of adhesive, to facilitate application. One or more indicia 48, such as numbers or text, may be also provided on the release backing 42 or on the exterior surface of the tape system or both, for example to provide instructions or to indicate the sequence of application.

As perhaps best shown in FIG. 1A, the first strip 50 has a palm anchor 52 comprising one or more segments, for example a palm anchor first segment 53 and a palm anchor second segment 54 meeting at a junction 56 and separated by a gap 55. The first strip 50 also has an anterior wrist portion 57, and extends to an anterior forearm anchor 58.

The first strip 50 is preferably dimensioned to fit the palm, wrist, and forearm of a person. For example, a palm anchor that is 2.75" long will fit most people since since 90% of men have a palm length between 3.9" and 4.6", and 90% of women have a palm length between 3.5" and 4.1". The forearm anchor should be long enough to fit the forearm of most people, for example a length between 3" and 4" will fit most people. The back of the hand is a little shorter so a back anchor that is 2" long will fit most people. The first strip can be about 2.5" wide, and the second strip can be about 2" wide, to fit most people. A second strip with a wrist anchor that is 10.25" long will wrap at least once around the wrist of most people, since 90% of men have a wrist circumference between 6.4" and 7.6", while 90% of all women have a wrist circumference between 5.4" and 6.4".

The second strip 60 has a back anchor 61 comprising one or more segments, for example a back anchor first segment 62 and a back anchor second segment 63 meeting at a junction 65 and separated by a gap 64. The second strip also includes a wrist anchor, indicated generally at 66, with a starting end 67, a central portion 68, and a finishing end 69.

Figure 2A:
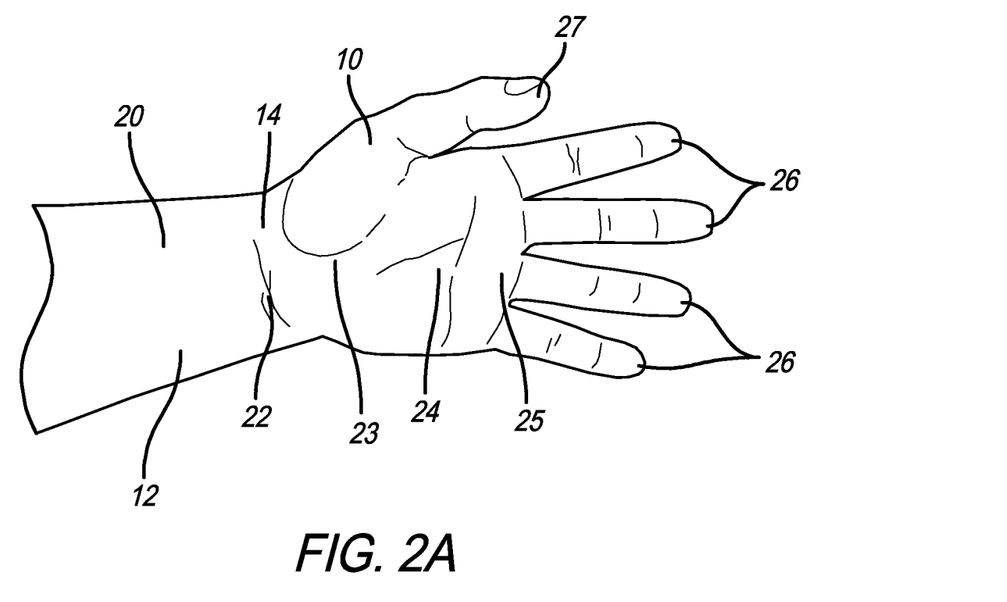
FIGS. 2A-2B are plan views of the anterior (palm side) forearm and hand, and posterior (back side) forearm and hand, respectively, of a person prior to application of the tape system of FIG. 1A.
Figure 2B:
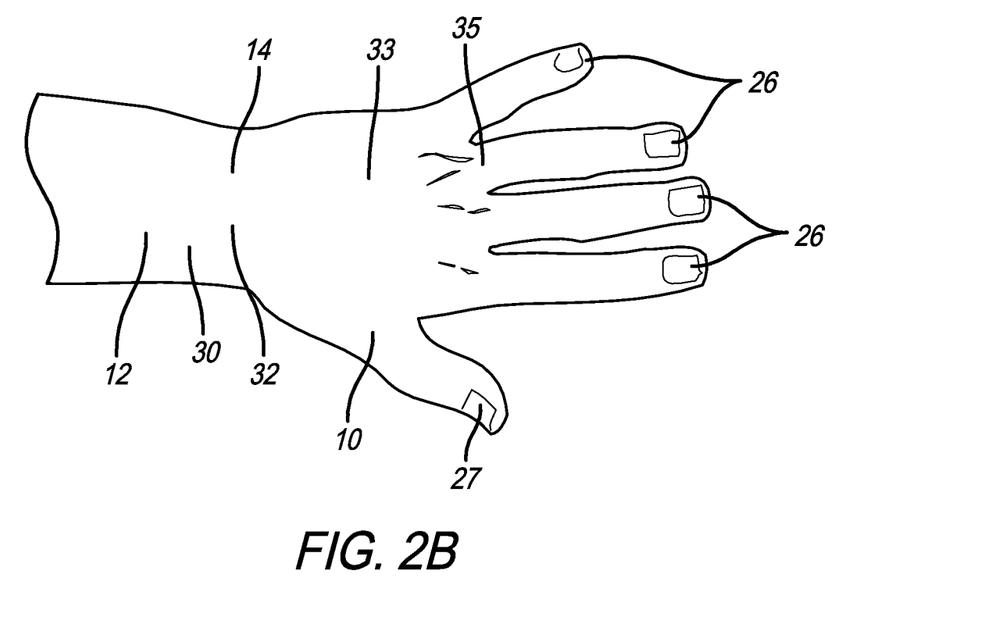

FIGS. 2A-2B show the front and back, respectively, of the hand 10, forearm 12, and wrist 14 of a person. As perhaps best shown in FIG. 2A, the forearm 12 includes an anterior forearm area 20 and an anterior wrist area 22. The hand 10 includes a heel 23, a palm central portion 24, and a palm perimeter 25 extending to fingers 26. As shown in FIG. 2B, the forearm 12 includes a posterior forearm area 30 and a posterior wrist area 32. The hand 10 has a back (the "hand-back") with a back central portion 33 that extends to a back perimeter 35.

Figure 3A:
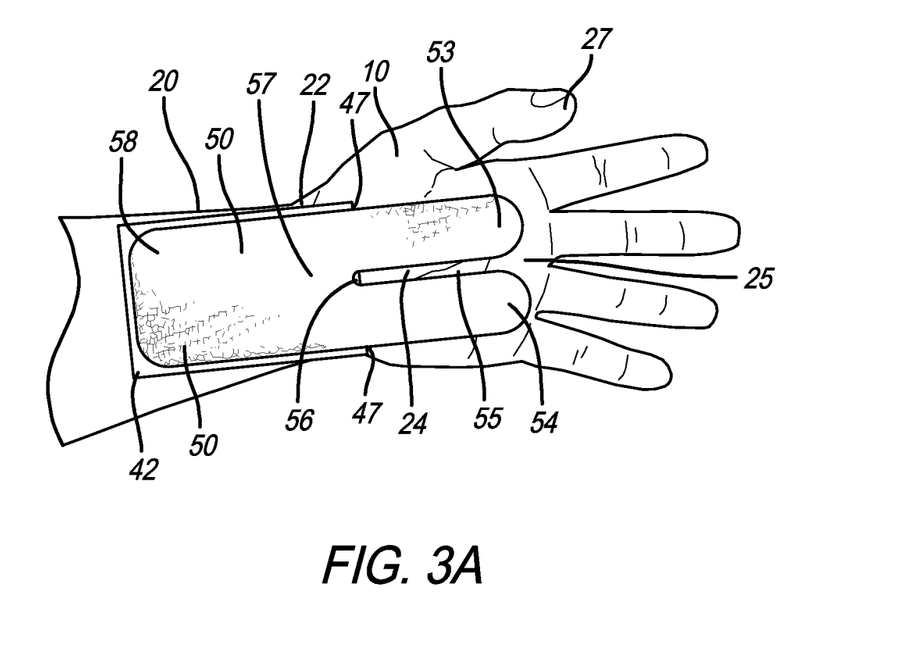
FIGS. 3A-3B are plan views of the anterior (palm side) forearm and hand, and posterior (back side) forearm and hand, respectively, of a person with the first strip partially applied, after adhering the palm anchor of the first strip to the palm of the wearer, but without adhering the anterior forearm anchor to the forearm of the wearer.
Figure 3B:
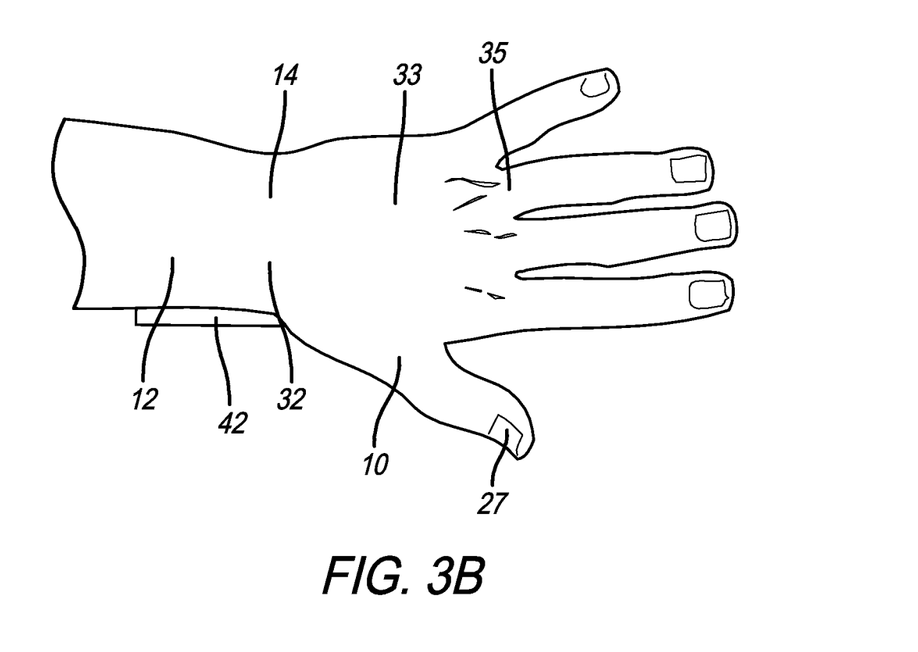

FIGS. 3A-3B show the first step in applying the tape system 40 to the wearer, preferably after washing and drying the wearer's skin in the area where the tape system 40 is to be applied. First, the release paper 42 covering the adhesive 43 on the palm anchor 52 of the first strip 50 is removed, without removing the adhesive 43 on the remainder of the first strip 50 (the anterior wrist portion 57 and anterior forearm anchor portion 58). The exposed adhesive 43 is then pressed against the palm central portion 24 of the wearer, to adhere the palm anchor 52 to the palm central portion 24. After this first step, release paper 42 still covers adhesive 43 on the anterior forearm anchor 58, and the anterior forearm anchor 58 is not adhered to the anterior forearm area 20 of the wearer.

Figure 4A:
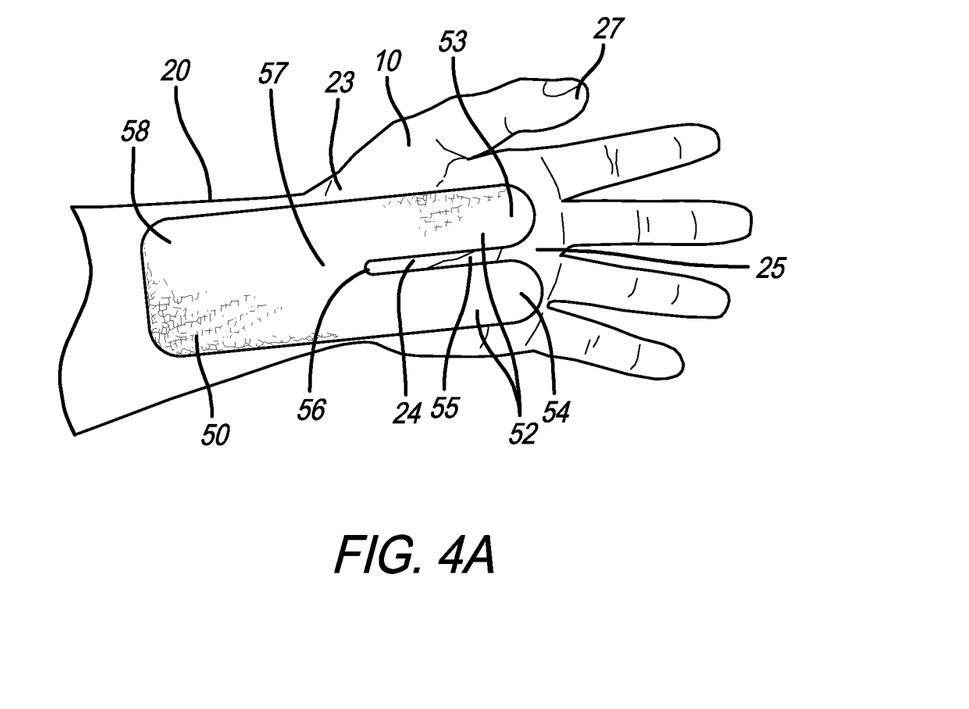
FIG. 4A is a plan view of the anterior (palm side) forearm and hand of a person with the first strip fully applied, after adhering both the palm anchor to the palm of the wearer and the anterior forearm anchor to the anterior forearm of the wearer.

FIG. 4A shows the second step in applying the tape system 40. After adhering the palm anchor 52 to the palm central portion 24 of the wearer in step 1, next the release paper 42 is removed to expose the adhesive 43 on the anterior forearm anchor 58. The exposed adhesive 43 is then pressed against the anterior forearm area 20 of the wearer, to adhere the anterior forearm anchor 58 to the anterior forearm area 20.

Figure 4B:
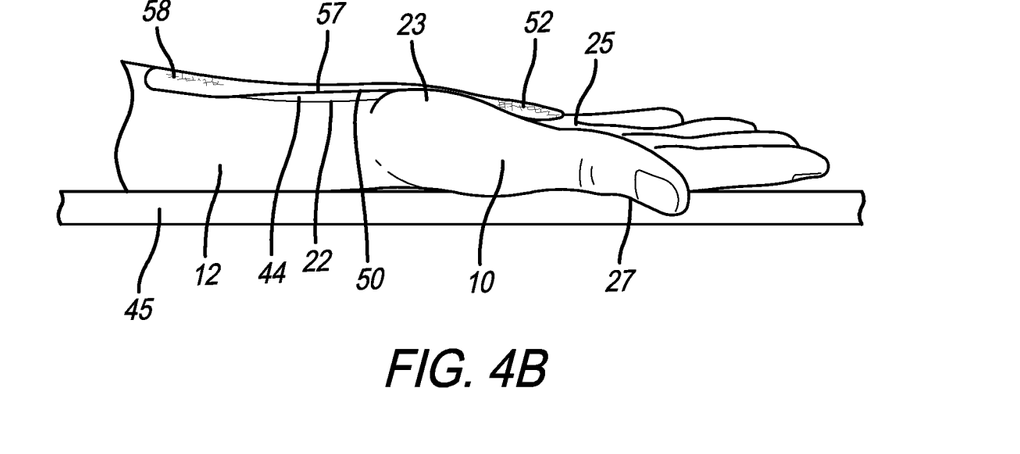
FIG. 4B is a side view of the forearm and hand of a person with the first strip fully applied, after adhering both the palm anchor to the palm of the wearer and the anterior forearm anchor to the anterior forearm of the wearer, presenting a side view instead of the plan view of FIG. 4A.

As perhaps best shown in FIG. 4B, after the first strip 50 is applied in this fashion, the anterior wrist portion 57 may be under a first tension, resulting in a gap 44 between the anterior wrist area 22 and the anterior wrist portion 57 of the first strip 40. This tension along the first strip 50 from the palm anchor 52 to the anterior forearm anchor 58, tends to resist extension (moving the palm away from the wrist) of the hand 10 relative to the forearm 12, and tends to immobilize the wrist against extension.

Figure 5A:
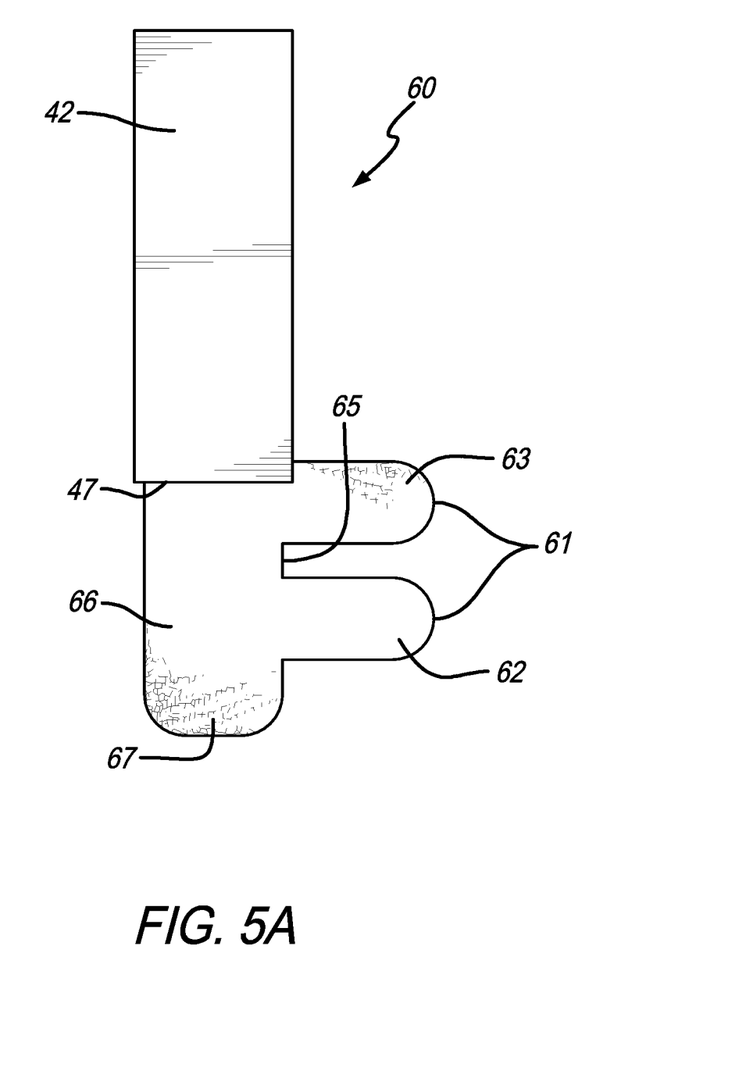
FIG. 5A is a plan view of the second strip laid flat on a table, with a portion of the release backing removed to expose the adhesive on the back anchor and on the starting end of the wrist anchor of the second strip.

FIG. 5A shows the third step in applying the tape system 40. After the first strip 50 has been fully applied to the palm and anterior forearm area of the wearer, the next step is to lay the second strip 60 flat on a table or other convenient horizontal surface, removing the release backing 42 covering the back anchor portion 61 (including the first segment 62 and second segment 63) and covering the wrist anchor starting end 37 to expose the adhesive 32 on those areas prior to application to the wearer.

Figure 5B:
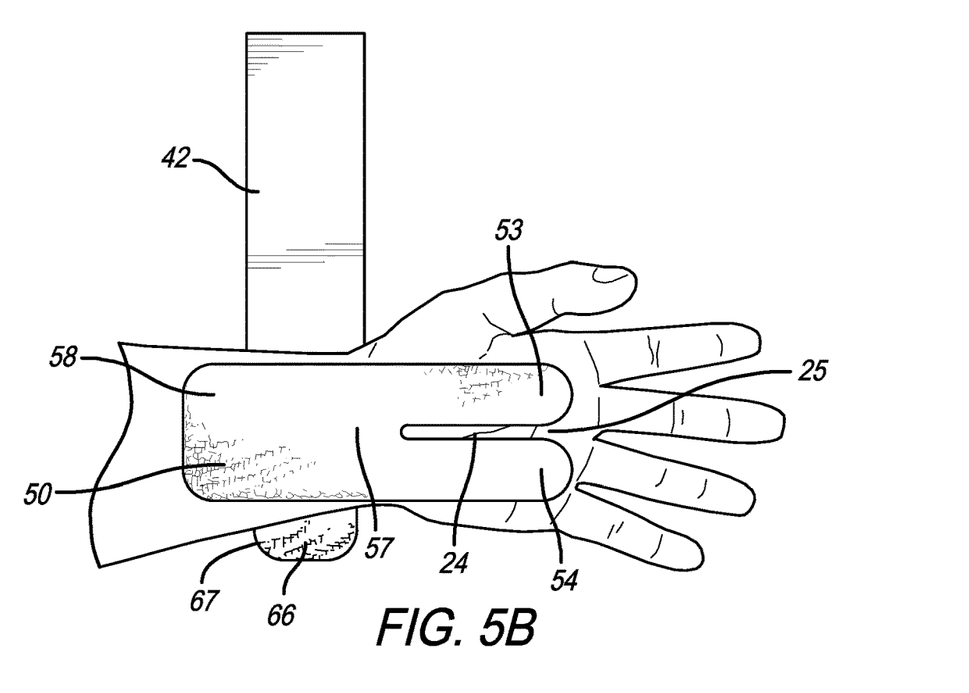
FIG. 5B is a plan view of the anterior (palm side) forarm and hand of a person with the first strip fully applied, with the back of the person's hand and posterior wrist area (not shown) pressed against the exposed adhesive on the back anchor and the starting end of the wrist anchor of the second strip.

With the second strip 60 flat as described, as shown in FIG. 5B the next step is to press the hand's back central portion 33 and the posterior wrist area 32 of the wearer against the exposed adhesive 43 on the back anchor portion 61 and wrist anchor starting end 67 of the second strip 60, to adhere those areas to the posterior wrist area 32 and hand back central portion 33 of the wearer. After this step, release paper 42 still covers adhesive 43 on the wrist anchor central portion 68 and wrist anchor finishing end 69 of the second strip 60, so those portions are not adhered to the wrist 14 of the wearer, as perhaps best shown in FIG. 5C.

Figure 5C:
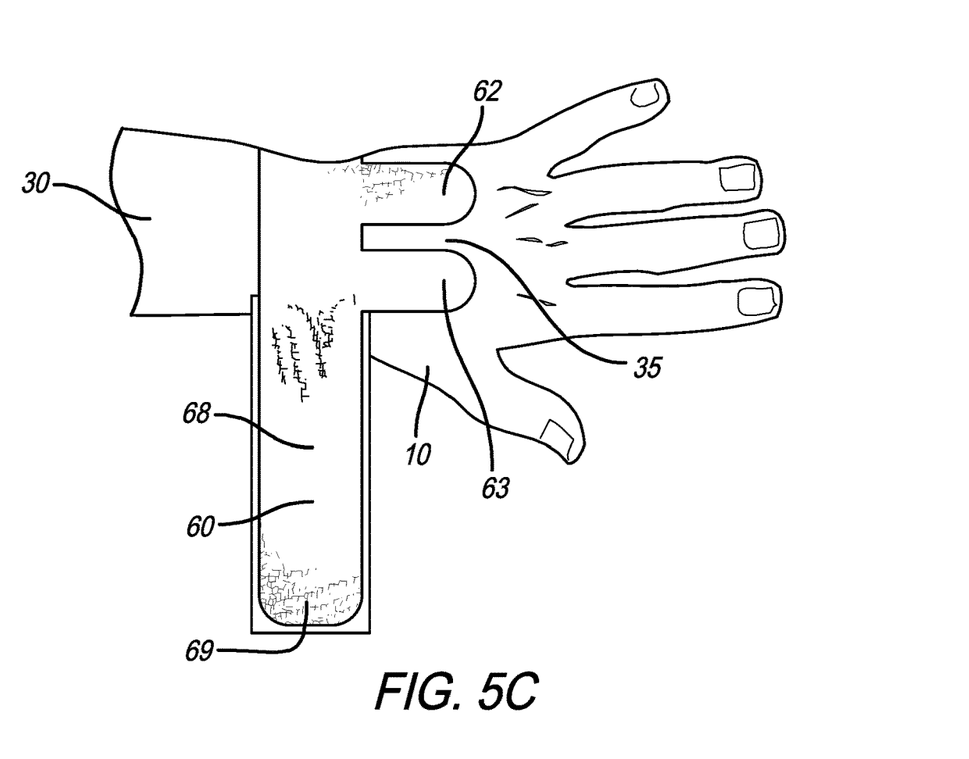
FIG. 5C is a plan view of the posterior (back side) portion of a person's forearm and hand, with the second strip partially applied by adhering the back anchor to the back of the person's hand and by adhering the exposed adhesive on the starting end of the wrist anchor to the posterior wrist area.

When the second strip 50 is applied in this fashion, the second strip 50 may be under a second tension between the back anchor 61 (including the first segment 62 and second segment 63) and the wrist anchor starting end 67. This tension along the second strip 50 tends to resist flexion (moving the palm toward from the wrist) of the hand 10 relative to the forearm 12, and tends to immobilize the wrist against flexion. The combination of the tension along the first strip 50 (that resists extension) and the tension along the second strip 60 (that resists flexion) tends to immobilize the wrist against both flexion and extension.

Figure 6A:
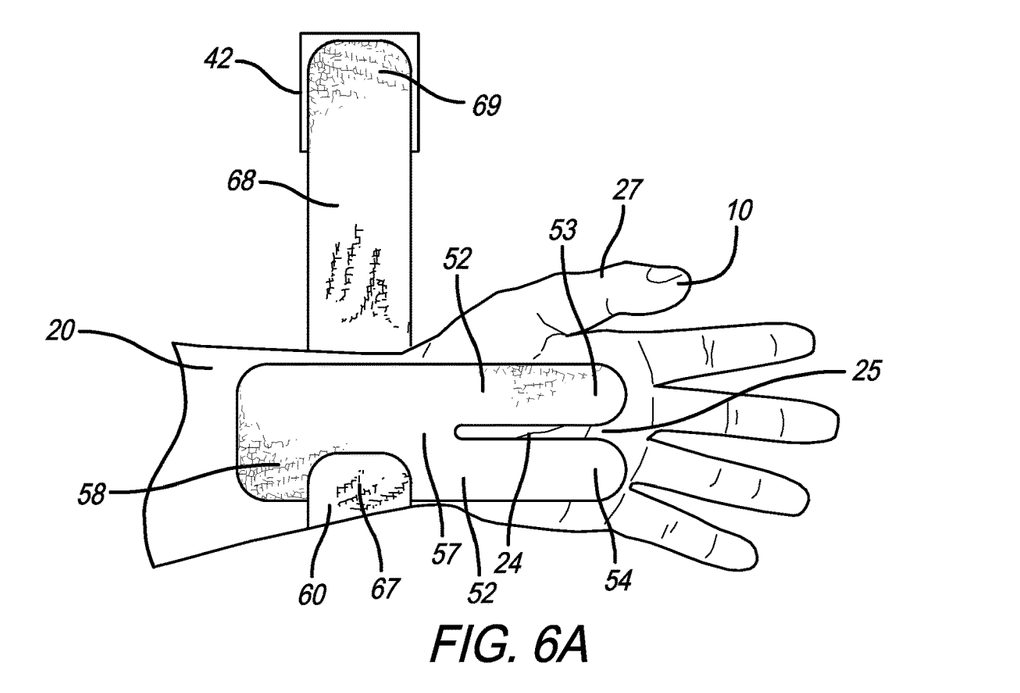
FIGS. 6A-6B are plan views of the anterior (palm side) forearm and hand, and posterior (back side) forearm and hand, respectively, of a person with the first strip fully applied and the second strip partially applied, after removing the release backing on the central portion of the wrist anchor, but before removing the release backing from the finishing end of the wrist anchor.
Figure 6B:
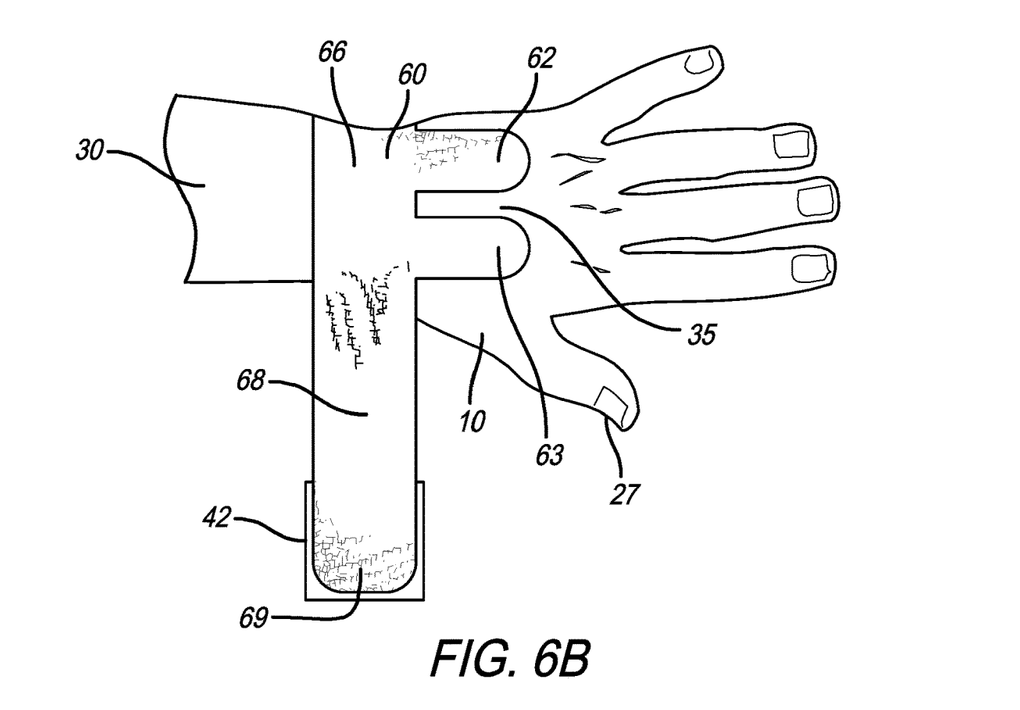
Figure 6C:
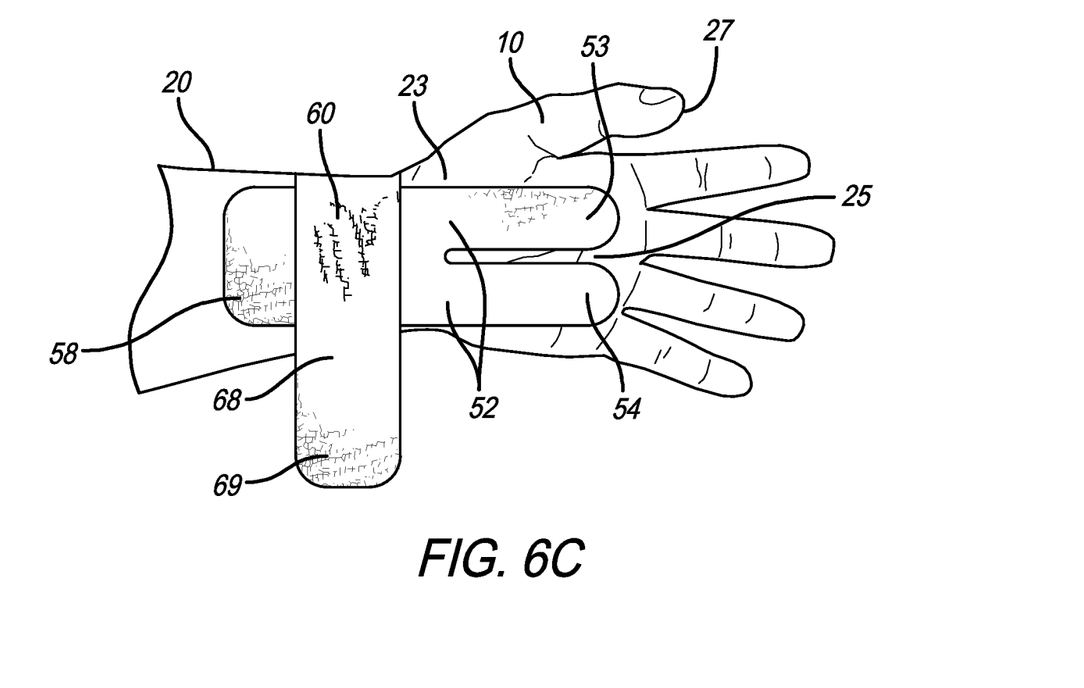
FIG. 6C is a plan view of the anterior (palm side) forearm and hand of a person with the first strip fully applied and the second strip partially applied and wrapped around the wrist once, after removing the release backing from the finishing end of the wrist anchor.

FIGS. 6A-6C show the final steps in applying the tape system 40. After the second strip 60 is partially applied according to the previous steps, next the remaining release paper 42 is removed to expose the adhesive 43 under the wrist anchor central portion 68 and the wrist anchor finishing end 69. Then the second strip 60 is wrapped around the wrist 14 of the wearer, pressing the wrist anchor central portion 68 to adhere to the wrist 14 until the wrist is completely wrapped and the wrist anchor finishing end is adhered in place. Importantly, the second strip 60 is preferably wrapped comfortably around the wrist, without wrapping so tightly that pressure is placed on the wrist that cuts off circulation or places pressure on the carpal tunnel. FIGS.

Figure 7A:
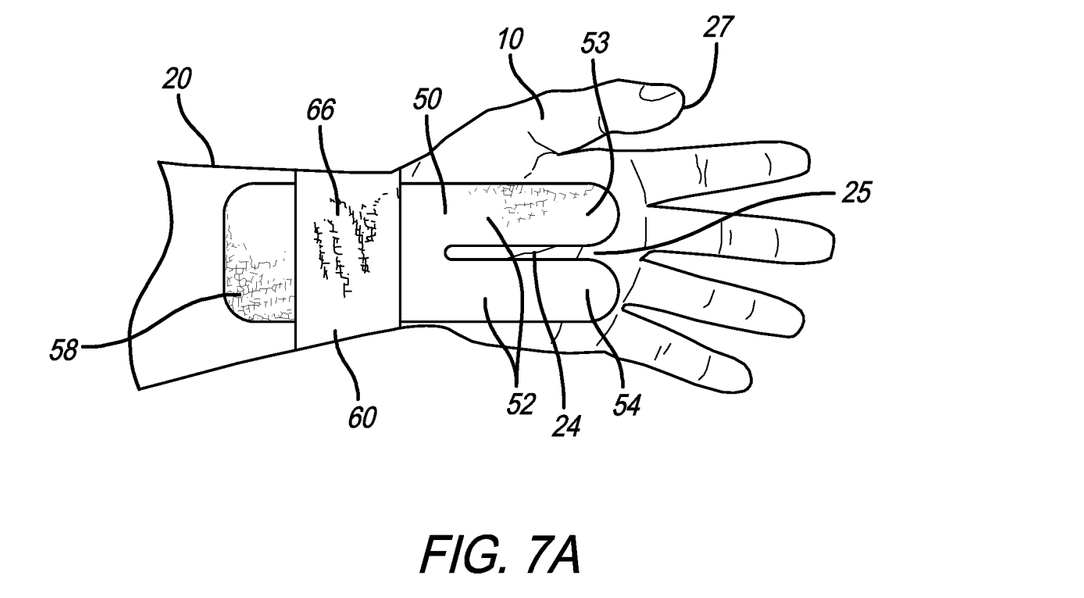
FIGS. 7A-7B are plan views of the anterior (palm side) forearm and hand, and posterior (back side) forearm and hand, respectively, of a person with the entire tape system (both the first strip and the second strip) fully applied and the second strip wrapped around the wrist with the finishing end adhered in place.
Figure 7B:
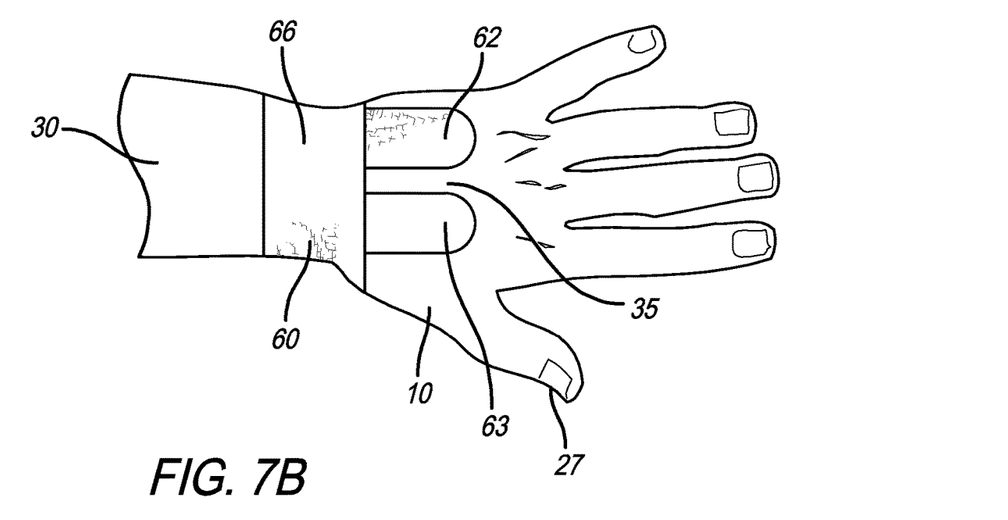

7A-7B show the tape system of FIG. 1A fully applied to the wrist and forearm of a person.

Figure 8:
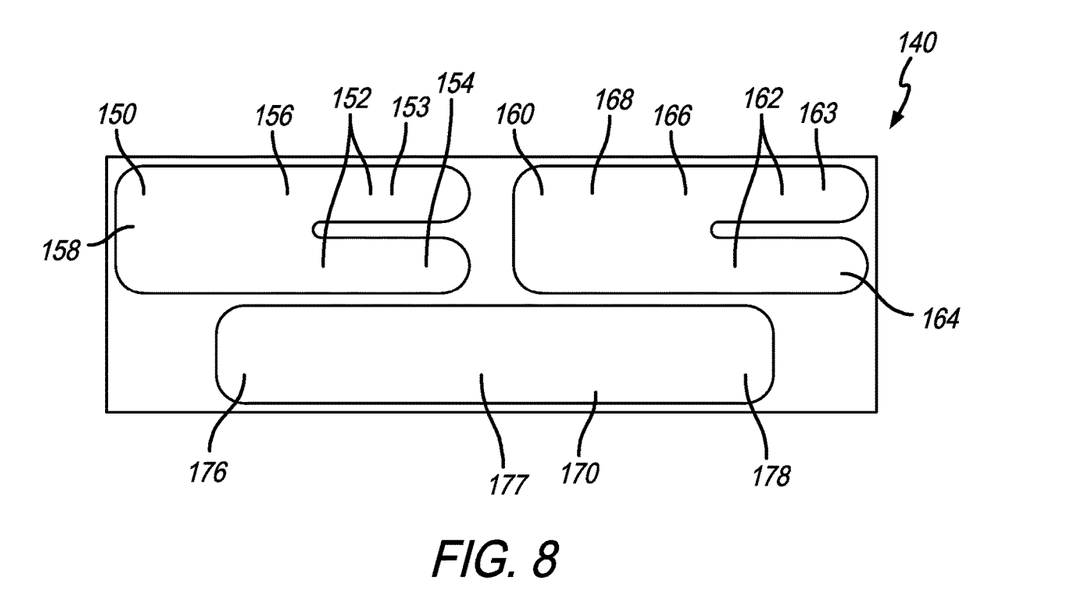
FIG. 8 is a plan view of an alternative disposable tape system for wrist immobilization according to the invention, laid flat to expose its exterior (front) surface.

FIG. 8 is a plan view of an alternative design 140 for a disposable tape system for wrist immobilization according to the invention, laid flat to expose its exterior (front) surface. The tape system 140 includes three pieces, a palm strip 150, a back strip 160, and a wrist strip 170. The palm strip 150 and back strip 160 may have the same shape, although this is not required. All three strips may be made on a single sheet of release paper, as shown in FIG. 8, but this is not required.

The palm strip 150 has a palm anchor 152, comprising one or more segments, for example a palm anchor first segment 153 and a palm anchor second segment 154, along with an anterior wrist portion 156 and an anterior forearm anchor 158. The back strip 160 has a back anchor 162, comprising one or more segments, for example a back anchor first segment 163 and a back anchor second segment 164, along with a posterior wrist portion 166 and a posterior forearm anchor 168. The wrist strip 170 has a starting end 167, a central portion 177, and a finishing end 178.

Figure 9A:
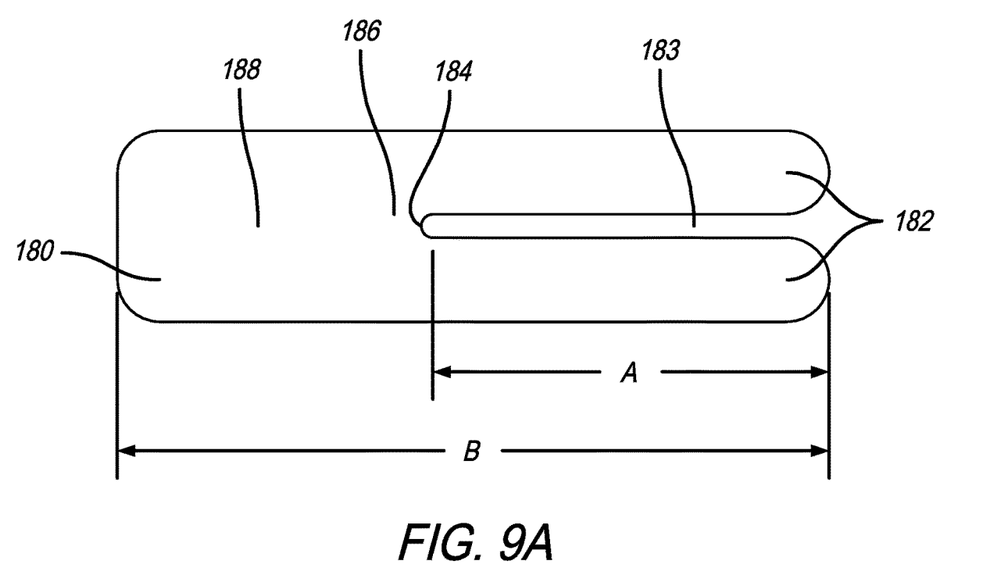
FIG. 9A is a plan view of an alternative first strip with elongated palm and/or anterior forearm anchor portions according to the invention, laid flat to expose its exterior (front) surface.

FIG. 9A is a plan view of an alternative first strip 180 with an elongated palm or back anchor. The strip 180 has an elongated anchor made of multiple elongated anchor segments 182 separated by one or more gaps 183 and meeting at one or more junctions 184. The strip 180 also has a wrist portion 186 and a forearm anchor 188.

Figure 9B:
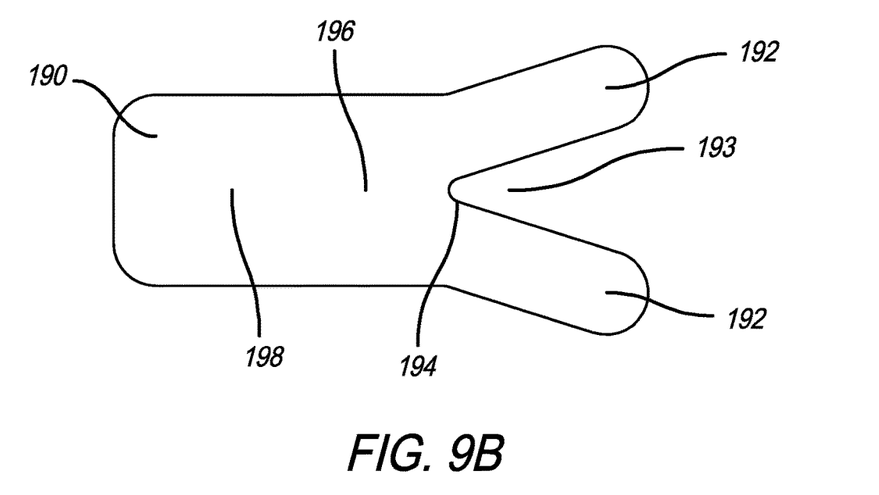
FIG. 9B is a plan view of an alternative first strip with V-shaped palm and/or anterior forearm anchor portions according to the invention, laid flat to expose its exterior (front) surface.

FIG. 9B is a plan view of an alternative first strip 190 with a V-shaped palm or back anchor. The strip 190 has an anchor made of multiple elongated anchor segments 192 separated by one or more V-shaped gaps 193 and meeting at one or more junctions 194. The strip 190 also has a wrist portion 196 and a forearm anchor 198.

Figure 10A:
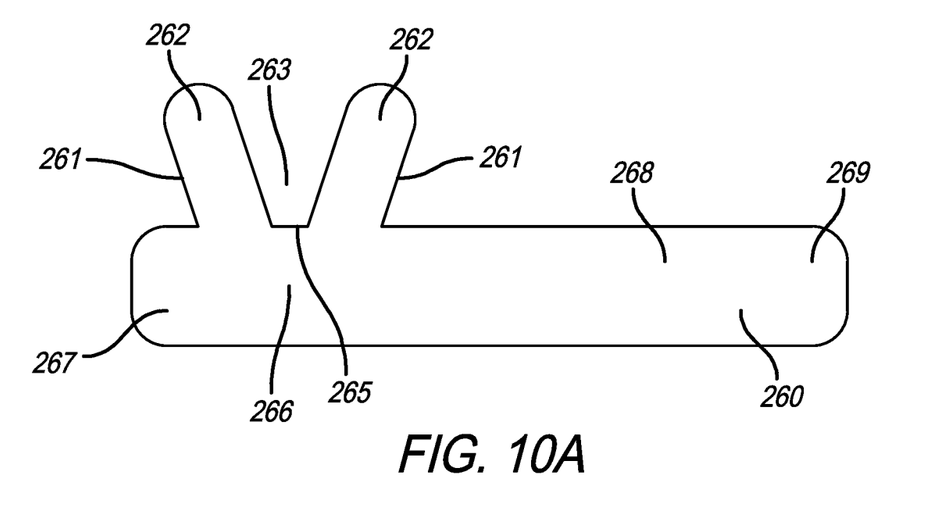
FIG. 10A is a plan view of an alternative second strip with a V-shaped back anchor according to the invention, laid flat to expose its exterior (front) surface.

FIG. 10A is a plan view of an alternative second strip 260 with a V-shaped back anchor. The strip 260 has a back anchor 261 made of multiple anchor segments 262 separated by a V-shaped gap 264 and meeting at a junction 265. The strip 260 includes a wrist anchor 266, with a starting end 267, a central portion 268, and a finishing end 269.

Figure 10B:
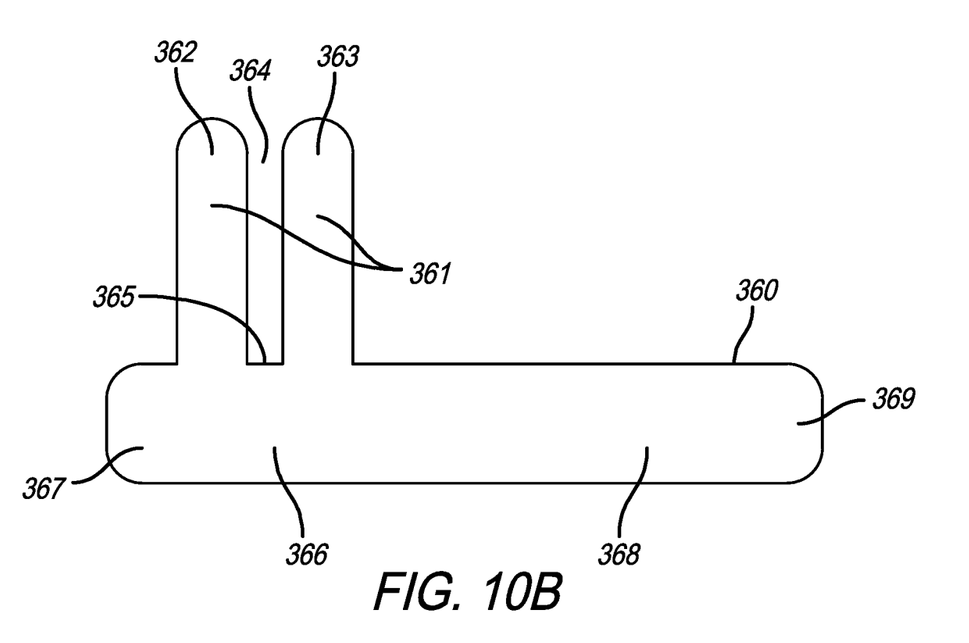
FIG. 10B is a plan view of an alternative second strip with an elongated back anchor according to the invention, laid flat to expose its exterior (front) surface.

FIG. 10B is a plan view of another alternative second strip 360 with an elongated anchor. The strip 360 has a back anchor 361 made of multiple elongated anchor segments 362 separated by a gap 364 and meeting at a junction 365. The strip 360 includes a wrist anchor 366, with a starting end 367, a central portion 368, and a finishing end 369.

It is understood that the invention is not confined to the embodiments set forth herein as illustrative, but embraces all such forms thereof that come within the scope of the following claims.

What is claimed is:

1. An tape kit for wrist immobilization, comprising:
   (a) a first strip formed of a first non-stretch flexible sheet material bearing adhesive and mounted on release backing, wherein the first strip includes a palm anchor portion adapted to fit the palm of a person with the palm anchor portion having a plurality of palm anchor segments separated by one or more palm anchor gaps, and an anterior wrist portion extending from the palm anchor portion to an anterior forearm anchor adapted to fit the forearm of a person; and
   (b) a second strip formed of a second non-stretch flexible sheet material bearing adhesive and mounted on release backing, wherein the second strip includes a back anchor portion adapted to fit the back of the hand of a person and having a plurality of back anchor segments separated by one or more back anchor gaps and a wrist anchor adapted to fit and wrap around the wrist area of a person and having a starting end adjacent to the wrist anchor, a wrist anchor central portion, and a wrist anchor finishing end.

2. The tape kit of claim 1 wherein the plurality of palm anchor segments consists of two palm anchor segments.

3. The tape kit of claim 1 wherein the plurality of palm anchor segments consists of more than two palm anchor segments.

4. The tape kit of claim 1 wherein the plurality of back anchor segments consists of two back anchor segments.

5. The tape kit of claim 1 wherein the plurality of back anchor segments consists of more than two back anchor segments.

6. The tape kit of claim 1 wherein the wrist anchor portion of the second strip is made of a cohesive flexible sheet material and the back anchor portion of the second strip bears adhesive.

7. A method of applying a tape kit for wrist immobilization, comprising:
   (a) providing a tape kit comprising (1) a first strip formed of a first non-stretch flexible sheet material bearing first adhesive and mounted on first release backing, wherein the first strip includes a palm anchor adapted to fit the palm of a person with the palm anchor portion having a plurality of palm anchor segments separated by one or more palm anchor gaps, and an anterior wrist portion extending from the palm anchor portion to an anterior forearm anchor adapted to fit the forearm of a person; and (2) a second strip formed of a second non-stretch flexible sheet material bearing second adhesive and mounted on second release backing, wherein the second strip includes a back anchor adapted to fit the hand-back of a person and having a plurality of back anchor segments separated by one or more back anchor gaps and a wrist anchor adapted to fit and wrap around the wrist area of a person and having a starting end adjacent to the wrist anchor, a wrist anchor central portion, and a wrist anchor finishing end;
   (b) removing the first release backing from the palm anchor of the first strip and then pressing the first adhesive on the palm anchor against a wearer's palm to adhere the palm anchor to the wearer's palm;
   (c) removing the first release backing from the anterior forearm anchor of the first strip, and then pressing the first adhesive on the anterior forearm anchor against a wearer's anterior forearm to adhere the anterior forearm anchor to the wearer's anterior forearm with the first strip having a first tension along the first strip from the palm anchor to the anterior forearm anchor;
   (d) applying the back anchor of the second strip against a wearer's hand-back, applying the wrist anchor starting end of the second strip to a wearer's posterior wrist area to introduce a second tension along the second strip from the back anchor to the wrist anchor; and
   (e) wrapping the second strip around the wearer's wrist to secure the wrist anchor about the wearer's wrist;
   whereby the first tension along the first strip from the palm anchor to the anterior forearm anchor tends to resist extension of the wearer's wrist and the second tension along the second strip from the back anchor to the wrist anchor tends to resist flexion of the wearer's wrist;
   whereby the combination of the first tension and the second tension tends to immobilize the wearer's wrist against both flexion and extension.

8. The method of claim 7 wherein the second flexible sheet material is a non-stretch flexible sheet material bearing a second adhesive and mounted on a second release backing, and step (d) includes a step of placing the second strip on a horizontal surface with the second adhesive on the back anchor facing up and exposed.

9. The method of claim 7 wherein the plurality of palm anchor segments consists of two segments.

10. The method of claim 7 wherein the plurality of palm anchor segments consists of more than two segments.

11. The method of claim 7 wherein the plurality of back anchor segments consists of two segments.

12. The method of claim 7 wherein the plurality of back anchor segments consists of more than two segments.

\* \* \* \* \*